United States Patent [19]
Kandler et al.

[11] Patent Number: 5,870,805
[45] Date of Patent: Feb. 16, 1999

[54] DISPOSABLE TUBING SET AND ORGANIZER FRAME FOR HOLDING FLEXIBLE TUBING

[75] Inventors: James J. Kandler, Lake Geneva, Wis.; Ahmad-Maher Moubayed, Mission Viejo, Calif.; Mark R. Vandlik, Gurnee, Ill.

[73] Assignee: Baxter International Inc., Deerfield, Ill.

[21] Appl. No.: 779,094

[22] Filed: Jan. 6, 1997

[51] Int. Cl.$^6$ ................................................. A44B 21/00
[52] U.S. Cl. ............................................................ 24/459
[58] Field of Search ........................... 27/335, 339, 545, 27/459; 248/68.1, 74.1, 74.3, 74.2, 74.4; 604/80

[56] References Cited

U.S. PATENT DOCUMENTS

| | | |
|---|---|---|
| D. 361,616 | 8/1995 | Tsuji . |
| 2,231,462 | 2/1941 | Cobb ..................................... 24/339 X |
| 3,374,509 | 3/1968 | Logan et al. . |
| 3,429,273 | 2/1969 | Jones et al. . |
| 3,709,222 | 1/1973 | DeVries . |
| 3,740,173 | 6/1973 | Natelson . |
| 3,832,096 | 8/1974 | Gelfand . |
| 3,876,340 | 4/1975 | Thomas . |
| 4,069,968 | 1/1978 | Herman . |
| 4,289,459 | 9/1981 | Neeley et al. . |
| 4,379,452 | 4/1983 | DeVries . |
| 4,473,342 | 9/1984 | Iles . |
| 4,526,515 | 7/1985 | DeVries . |
| 4,824,339 | 4/1989 | Bainbridge . |
| 4,886,431 | 12/1989 | Soderquist et al. . |
| 5,029,782 | 7/1991 | Andre et al. ........................ 248/74.4 X |
| 5,096,393 | 3/1992 | Van Steenderen . |
| 5,098,261 | 3/1992 | Bertonicini . |
| 5,224,674 | 7/1993 | Simons ................................... 248/68.1 |
| 5,443,451 | 8/1995 | Chapman et al. . |
| 5,460,493 | 10/1995 | Deniega et al. . |

FOREIGN PATENT DOCUMENTS

| | | |
|---|---|---|
| 2 396 880 | 2/1979 | France . |
| WO 95/24969 | 3/1995 | WIPO . |

*Primary Examiner*—James R. Brittain
*Attorney, Agent, or Firm*—Andrew G. Kolomayets; Denise M. Serewicz; Bardford R. L. Price

[57] ABSTRACT

A disposable tubing set having an array of flexible tubing and a method for holding an array of flexible tubing. The disposable tubing set has a frame for holding segments of the tubing. The frame includes at least two sides and a plurality of apertures defined in the sides. Segments of the tubing extend through and are completely enclosed by the apertures.

17 Claims, 12 Drawing Sheets

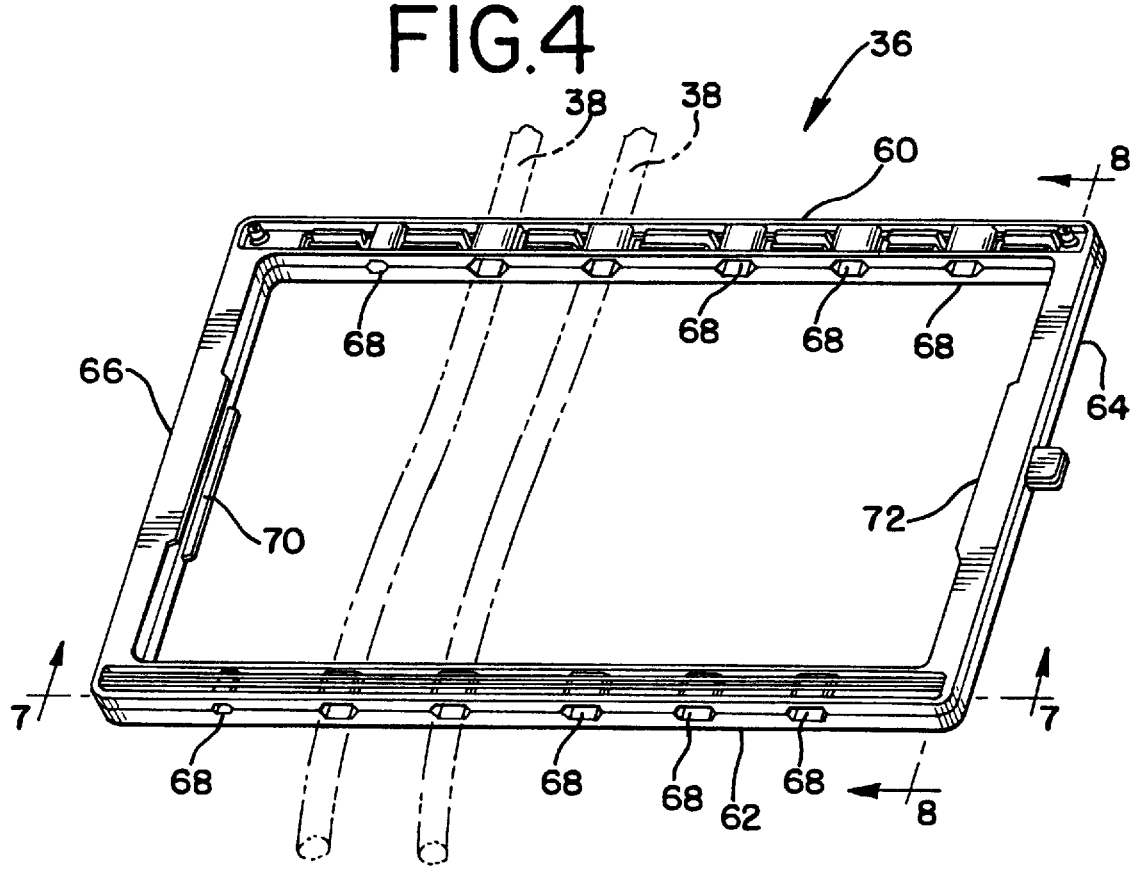
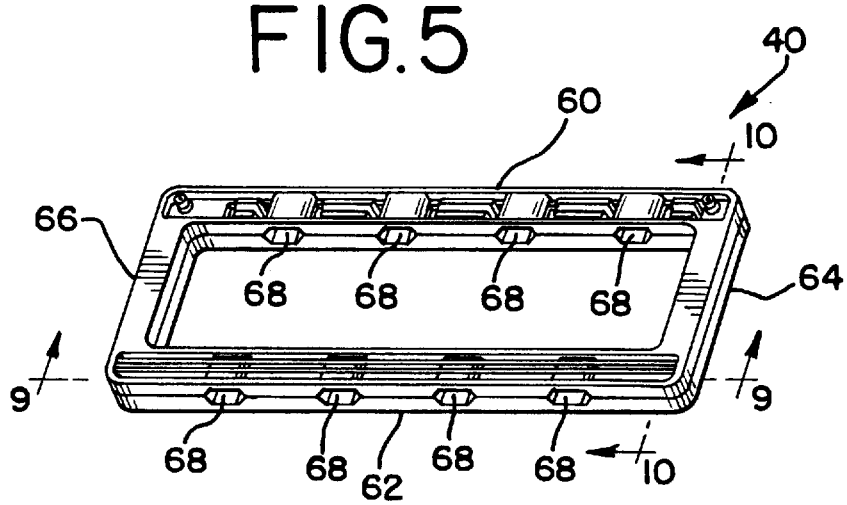

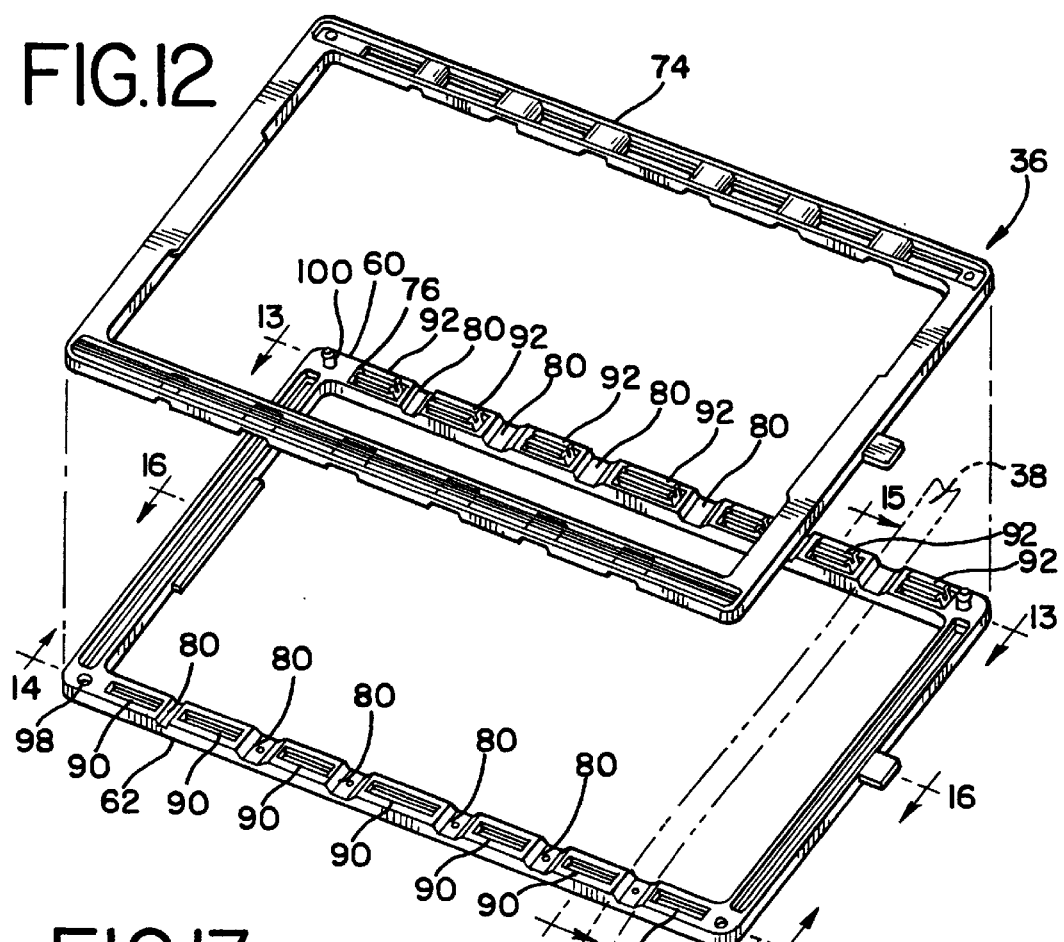
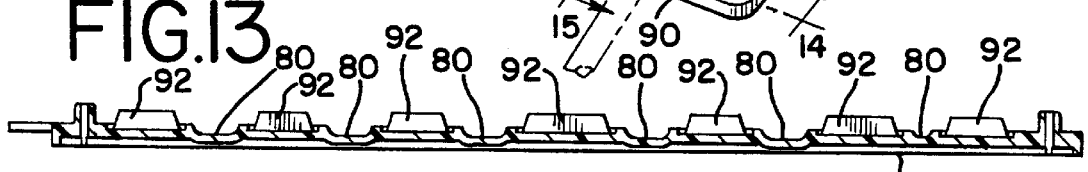
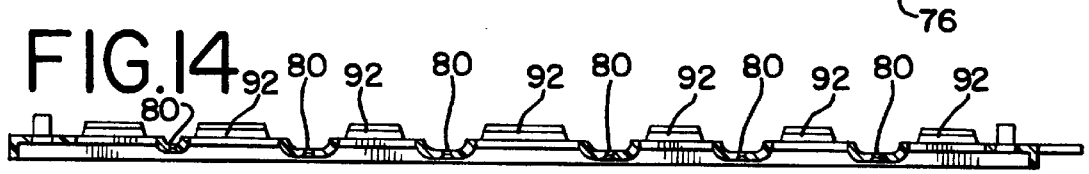
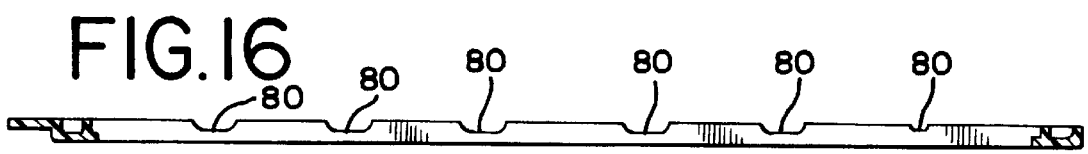

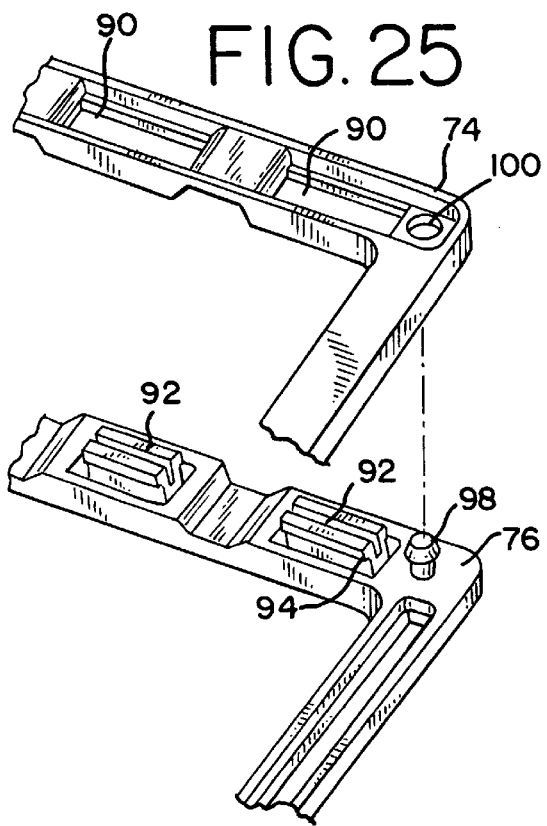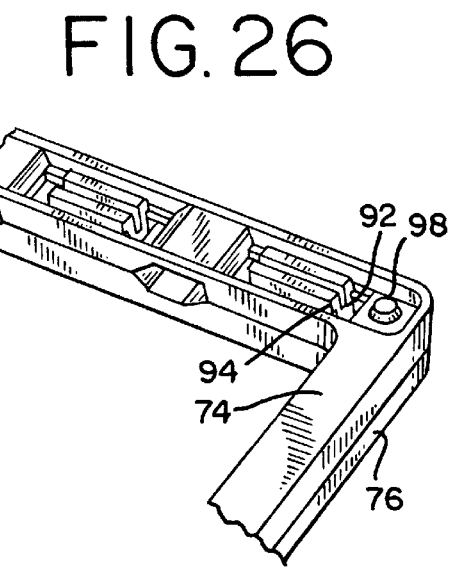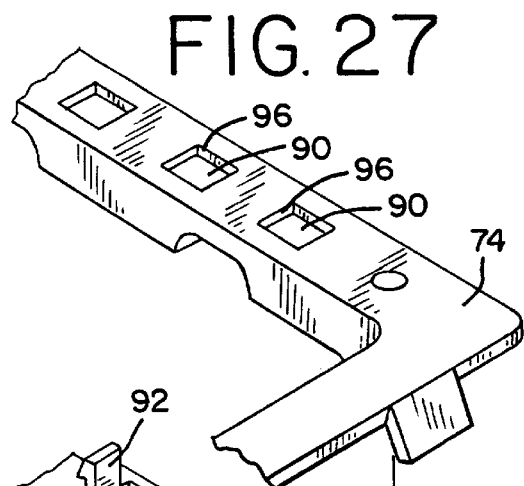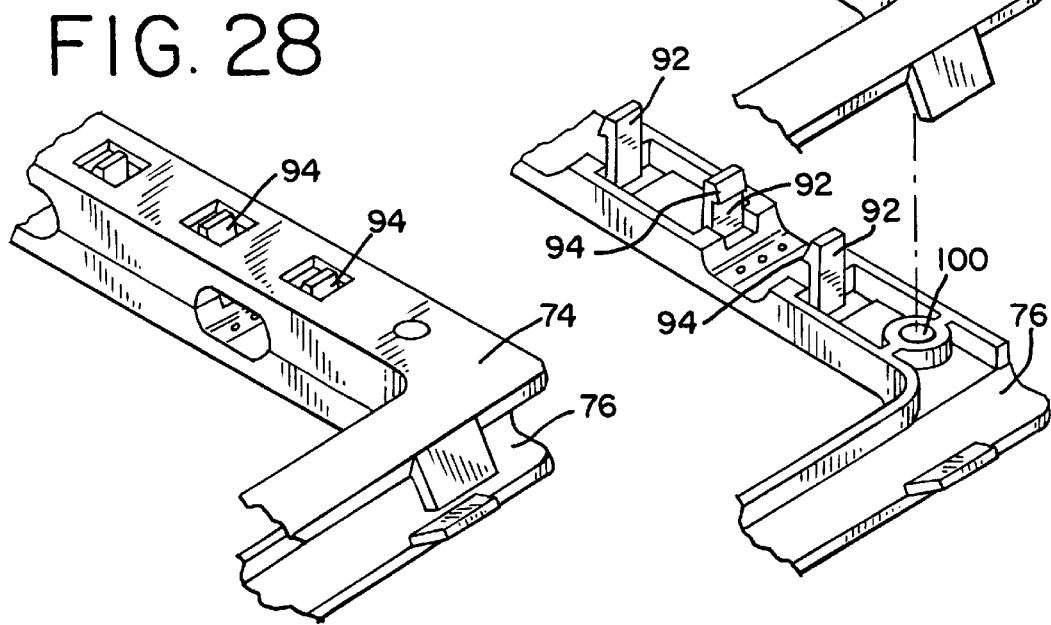

DISPOSABLE TUBING SET AND ORGANIZER FRAME FOR HOLDING FLEXIBLE TUBING

The present invention relates generally to apparatus for separating suspensions including cell components, such as blood, into one or more components. More particularly, the present invention relates to a disposable tubing set for use with apparatus.

BACKGROUND OF THE INVENTION

Hemapheresis refers to the separation of blood into one or more of its components or fractions such as red cells, white cells, platelets and plasma. In typical hemapheresis procedures, whole blood is withdrawn from a donor or patient, anticoagulant is added to the withdrawn whole blood and one or more desired components or fractions are separated from the anticoagulated whole blood.

In hemapheresis procedures, blood is withdrawn from a donor or patient through a needle that is inserted into the vein of the donor or patient. The needle communicates with tubing through which the blood flows (often with the aid of pumps) to a device that separates the blood into its components or fractions. The separation device is often housed in an instrument that controls and regulates many aspects of the hemapheresis procedure (e.g. flow rates). Hemapheresis procedures and systems that utilize an instrument and/or device that separates blood into its components without significant operator intervention are often referred to as "automated" procedures and systems.

Instruments used to perform automated hemapheresis procedures typically include a reusable hardware portion and a disposable tubing portion intended for one-time use only. The hardware portion may include pumps, such as peristaltic pumps for (1) withdrawing whole blood from a donor or patient, (2) introducing blood or blood components into a separation device for separating blood into its components and (3) withdrawing one or more blood components from the separation device for subsequent use or for return to the donor or patient. Either the hardware portion or the disposable tubing portion may include the separation device which, for example, can be a rotating centrifuge as described in U.S. Pat. No. 4,146,172 or a rotating membrane as described in U.S. Pat. No. 4,753,729.

The disposable tubing portion typically includes, among other things, the plastic tubing which transports the blood and/or blood components to and from the donor or patient and to and from the separation device. If a desired blood component is to be collected, the disposable tubing portion may also include plastic bags for collecting the desired blood component(s). Typically, the segments of the tubing are threaded over and engaged by the peristaltic pumps of the instrument. Peristaltic pumps include rotating members (rotors) driven by motors. Rotation of the pump rotors squeezes the tubing and consequently draws and pushes the blood or blood components through the tubing and through the system.

In the early days of automated hemapheresis, tubings of the disposable set were threaded over the individual pump rotors one at a time by the instrument operator. For example, in the Aminco (later Fenwal) Celltrifuge® Blood Cell Separator, tubing segments were individually threaded over six peristaltic pump rotors. Similarly, in the IBM/Cobe 2997, the individual tubing segments were threaded over six pump rotors. This required great care on the part of the operator who had to ensure that the correct tubing segment was mated with the correct pump rotor and that the tubing was properly loaded onto the particular pump, thus, significantly adding to the time required to "set-up" the hemapheresis instrument.

More recently, efforts have been made to reduce the required set-up time of the hemapheresis instrument. Several of the currently commercially available automated hemapheresis instruments utilize disposable sets which have combined the tubing in prepackaged modules, which may include housings through which the tubing is routed, or other means which allow the tubing segments to be quickly and correctly mated with the proper pump rotor. Placement of the module, housing or other means (containing the tubing segments) on the hemapheresis instrument results in simultaneous placement of the tubing segments over the respective pump rotors and ensures that the correct tubing segment is mated with the appropriate pump rotor.

One example of such a prepackaged module with integral tubing segments is the one used with the CS3000 (and CS3000 Plus) made and sold by Baxter Healthcare Corporation of Deerfield, Ill. and described in U.S. Pat. No. 4,526,515 to DeVries (which is assigned to the assignee of the present application.) That patent describes a prepackaged fluid circuit module which includes a housing that can be removably positioned on a hemapheresis instrument in a predetermined relationship with respect to pump rotors. Tubing loops extending from the housing are disposed to interfit with selected pump rotors.

A similar device is used by the Cobe Spectra sold by Cobe Laboratories, Inc. of Lakewood, Colo. and described in U.S. Pat. No. 4,824,339 to Bainbridge. That patent describes a pump housing or cartridge having continuous flexible tubing with U-shaped loops integral with the housing. The tubing loops mate with specific peristaltic pump rotors on the face of the Spectra instrument.

Another example of a disposable tubing set that includes an apparatus for holding tubing segments is the set used with the Mini-Autopheresis-C®, also made and sold by Baxter Healthcare Corporation and described in, for example, U.S. Pat. No. 5,460,493 (which patent is also assigned to the assignee of the present application and which is incorporated by reference herein.) There, the disposable tubing set includes a tubing "organizer" in the form of a plastic rectangular frame. The frame is provided with slots for holding various tubing segments in a desired orientation. The frame is placed on the face of the instrument in such a way that the tubing segments are mated with particular pump rotors located on the face of the instrument. Another portion of the frame holds other tubing segments of the disposable tubing set in place so that when the frame is placed on the instrument, those tubing segments are mated with specific clamping devices on the instrument.

The tubing organizer described in U.S. Pat. No. 5,460,493 provides an efficient and inexpensive way of reducing the set-up time of the hemapheresis instrument. The disposable tubing set is preassembled at a factory where the tubing segments are manually inserted into the appropriate slots. As shown in the top figure of FIG. 11 of U.S. Pat. No. 5,460,493, the circular slots of the organizer frame include openings to allow the tubing to be inserted into the slots. However, because the openings are smaller than the diameter of the tubing, the tubing segments must be stretched, pinched and pushed into the slot to ensure proper placement. Occasionally, if the tubing has not been firmly placed within the slot, the tubing segment may become dislodged from the slot (leaving it to the hemapheresis instrument operator to reinsert the tubing into the appropriate slots) or the tubing may remain partially pinched or occluded.

Accordingly, the present invention is directed to a disposable tubing set having an organizer frame which includes the benefits of the earlier tubing organizer frame and improves the ease of assembly by eliminating the need to pinch, stretch and push the tubing into place. The present invention also improves the reliability of the frame by minimizing the risk that the tubing segments will become dislodged prior to use or pinched by the organizer frame.

SUMMARY OF THE INVENTION

The present invention is directed to a disposable tubing set. The tubing set includes an array of flexible tubing segments and a frame for holding the tubing. The frame comprises first and second opposed sides and a plurality of apertures defined in the first and second sides. The tubing segments extend through the apertures and are completely enclosed by the apertures.

The present invention is also directed to a method for holding an array of flexible tubing. The method includes providing first and second frame portions, each of the frame portions having among other things, a first side and a second side. Each of the sides of the frame portions has an inner surface with recesses spaced thereon. In accordance with the method of the present invention, segments of tubing are located between the inner surfaces of the first and second frame portions so that the tubing segments are disposed within the recesses of the frame portions. The first and second frame portions are joined whereby the recesses of the first and second frame portions are in registration and, thus, form closed apertures around the tubing segments.

BRIEF DESCRIPTION OF THE DRAWINGS

FIG. 4 is a perspective view of the tubing organizer embodying the present invention;

FIG. 5 is a perspective view of another tubing organizer embodying the present invention;

FIG. 12 is an exploded perspective view of the tubing organizer of FIG. 4;

FIG. 13 is a cross-sectional side view of one portion of the tubing organizer of FIG. 12 taken along 13—13;

FIG. 14 is a cross-sectional side view of one portion of the tubing organizer of FIG. 12 taken along 14—14;

FIG. 15 is a cross-sectional view of one portion of the tubing organizer of FIG. 12 taken along 15—15;

FIG. 16 is a cross-sectional view of one portion of the tubing organizer of FIG. 12 taken along 16—16;

FIG. 25 is an enlarged exploded partial perspective view of the tubing organizer embodying the present invention;

FIG. 26 is a partial perspective view of the tubing organizer of FIG. 25;

FIG. 27 is an enlarged exploded partial perspective view of an alternative tubing organizer embodying the present invention; and FIG. 28 is a partial perspective view of the alternative tubing organizer of FIG. 27.

DETAILED DESCRIPTION OF THE DRAWINGS

Figure 1:
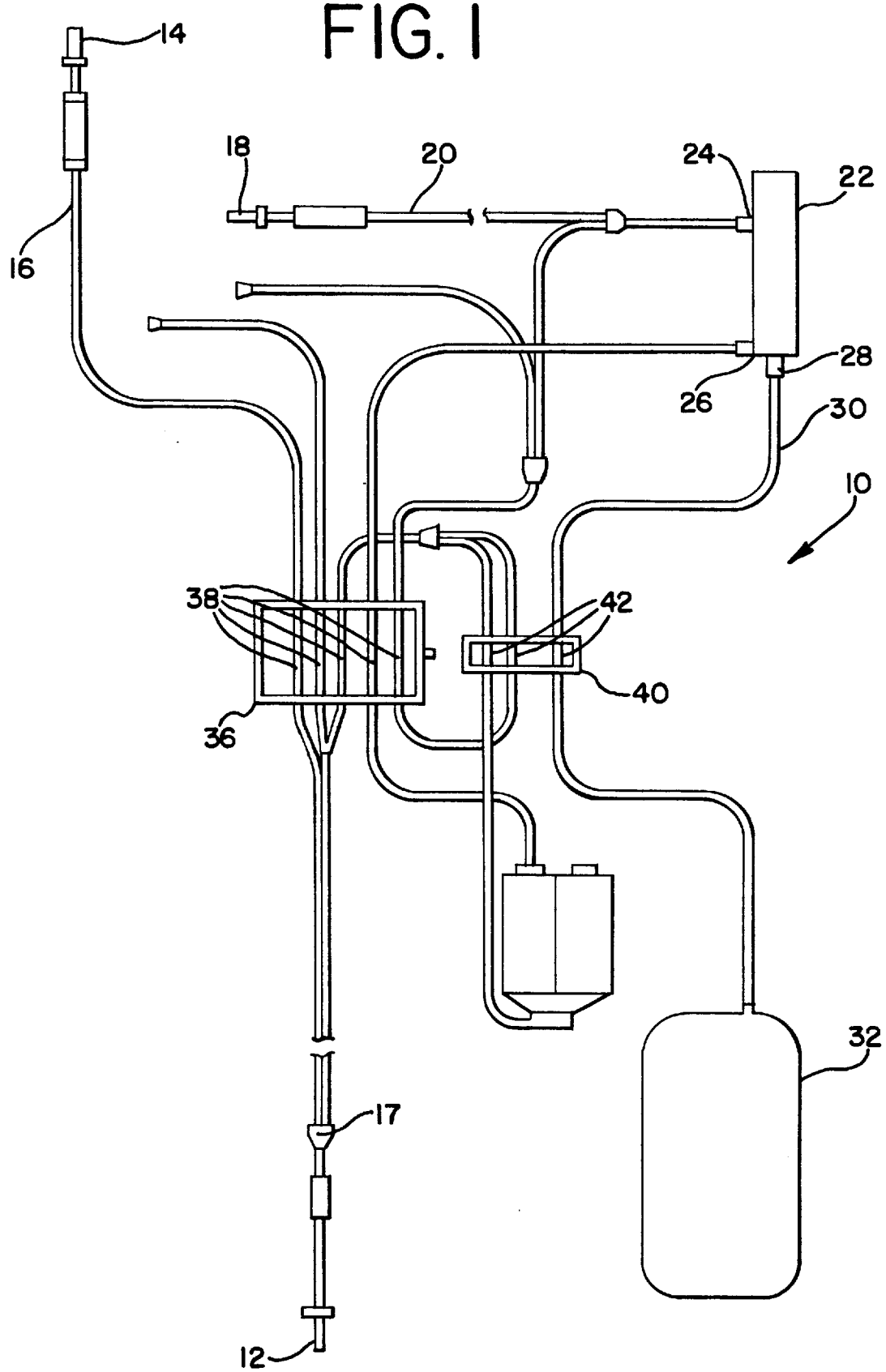
FIG. 1 is a top plan view of a disposable tubing set with tubing organizers embodying the present invention.

Turning now to the drawings, a disposable tubing set 10 in accordance with the present invention is shown in FIG. 1. Disposable tubing set 10 may be used in combination with a hemapheresis apparatus, described in more detail hereafter, for separating and collecting red cells, white cells, platelets or plasma from whole blood. It should be understood, however, that the disposable tubing sets of the present invention are not limited to the collection of any particular blood component or even to hemapheresis. The disposable tubing set of the present invention may be used with any method or system that uses an array of tubing that must be placed on an instrument in a predetermined fashion.

In one embodiment related to hemapheresis (e.g. FIG. 1), tubing set 10 includes, for example, venepuncture needle 12 for withdrawing whole blood from a donor or a patient. An anticoagulant spike 14, which is attached to anticoagulant tubing line 16, is provided for attachment to a source of anticoagulant (not shown) for mixing with the blood. The anticoagulant line communicates with whole blood inlet tubing line via standard Y-site or V-site 17. Disposable tubing set 10 also includes saline spike 18 attached to saline tubing line 20. Saline is used to prime the disposable tubing set, displace air in the disposable tubing set and, in those procedures where plasma is removed and not returned to the donor or patient, to replenish the donor's or patient's circulatory system with liquid.

Disposable tubing set 10 shown in FIG. 1 also includes a separator 22 for separating anticoagulated whole blood into packed cells (e.g. red cells, white cells, platelets) and plasma. Separator 22 has an anticoagulated whole blood inlet port 24, a packed cell outlet port 26 and a platelet-poor plasma outlet port 28. Plasma line 30 extends from platelet-poor plasma port 28 to container 32 which is used for collecting separated plasma. Additional details of the disposable tubing set and the components thereof are set forth in U.S. Pat. Nos. 5,034,135 and 5,460,493, which are incorporated by reference herein.

Disposable tubing set 10 also includes a tubing organizer 36 in accordance with the present invention. As shown in FIG. 1, tubing organizer 36 holds tubing segments 38 of tubing set 10 in a specific orientation. Disposable tubing set 10 includes a second tubing organizer 40 which holds different tubing segments 42.

Figure 1A:
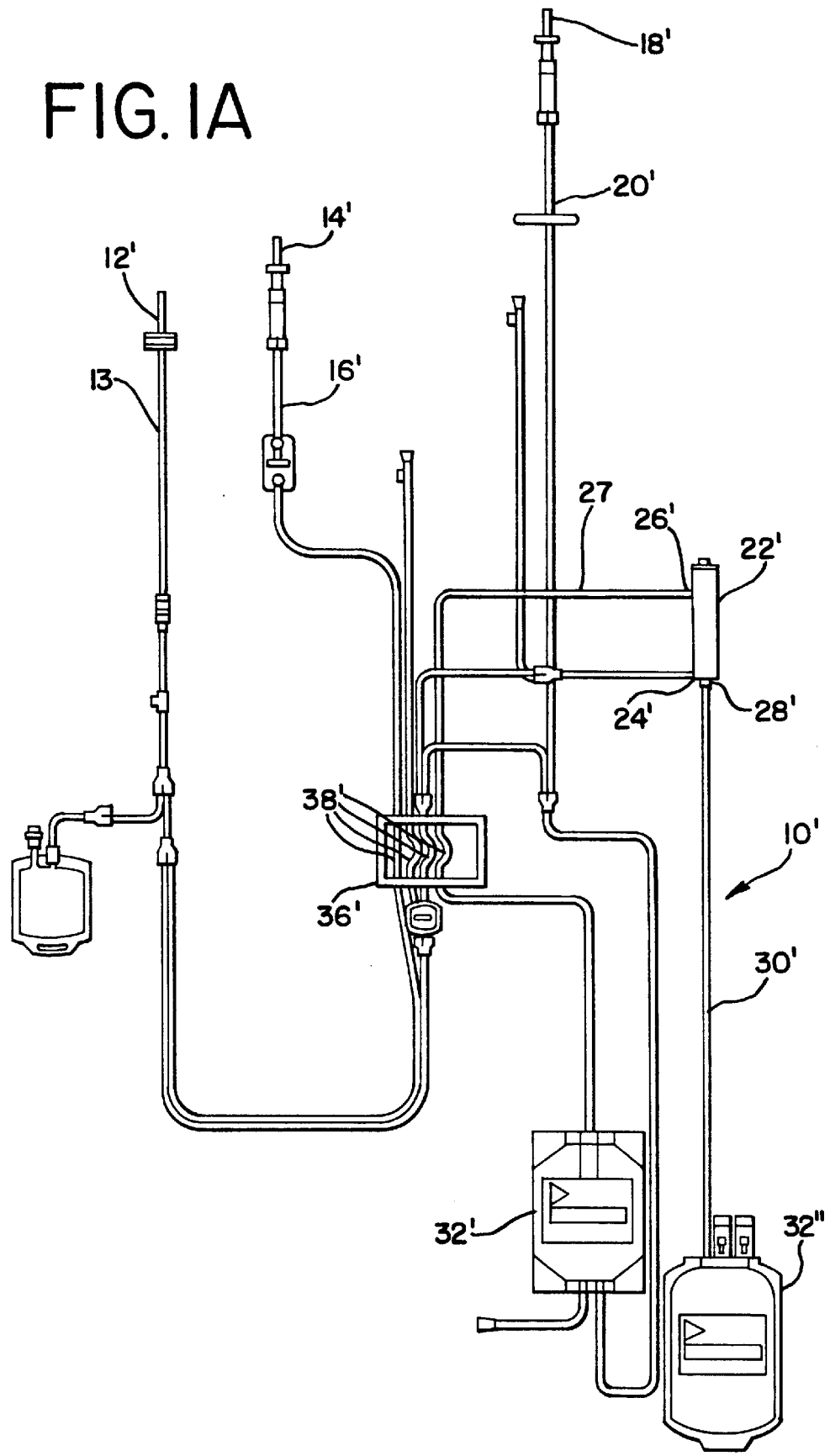
FIG. 1A is a top plan view of an alternative disposable tubing set with a tubing organizer embodying the present invention.

FIG. 1A shows an alternative disposable tubing set 10' for use in collecting red cells and/or plasma separated from whole blood. As with the disposable tubing set 10 shown in FIG. 1, tubing set 10' of FIG. 1A includes a venepuncture needle 12', attached to whole blood inlet tubing line 13, and an anticoagulant spike 14' attached to anticoagulant tubing line 16'. Disposable tubing set 10' includes a saline spike 18', saline line 20' and a separation device 22'. As shown in FIG. 1A, separation device 22' includes a whole blood inlet port 24', packed cell port 26' in communication with packed cell line 27 and platelet-poor plasma port 28' in communication with platelet-poor plasma line 30'. As shown in FIG. 1A, lines 27 and 30' are attached to containers 32' and 32" respectively for collecting red blood cells (32') and plasma (32"). Disposable tubing set 10' includes a single tubing organizer 36' for holding tubing segments 38'.

Figure 2:
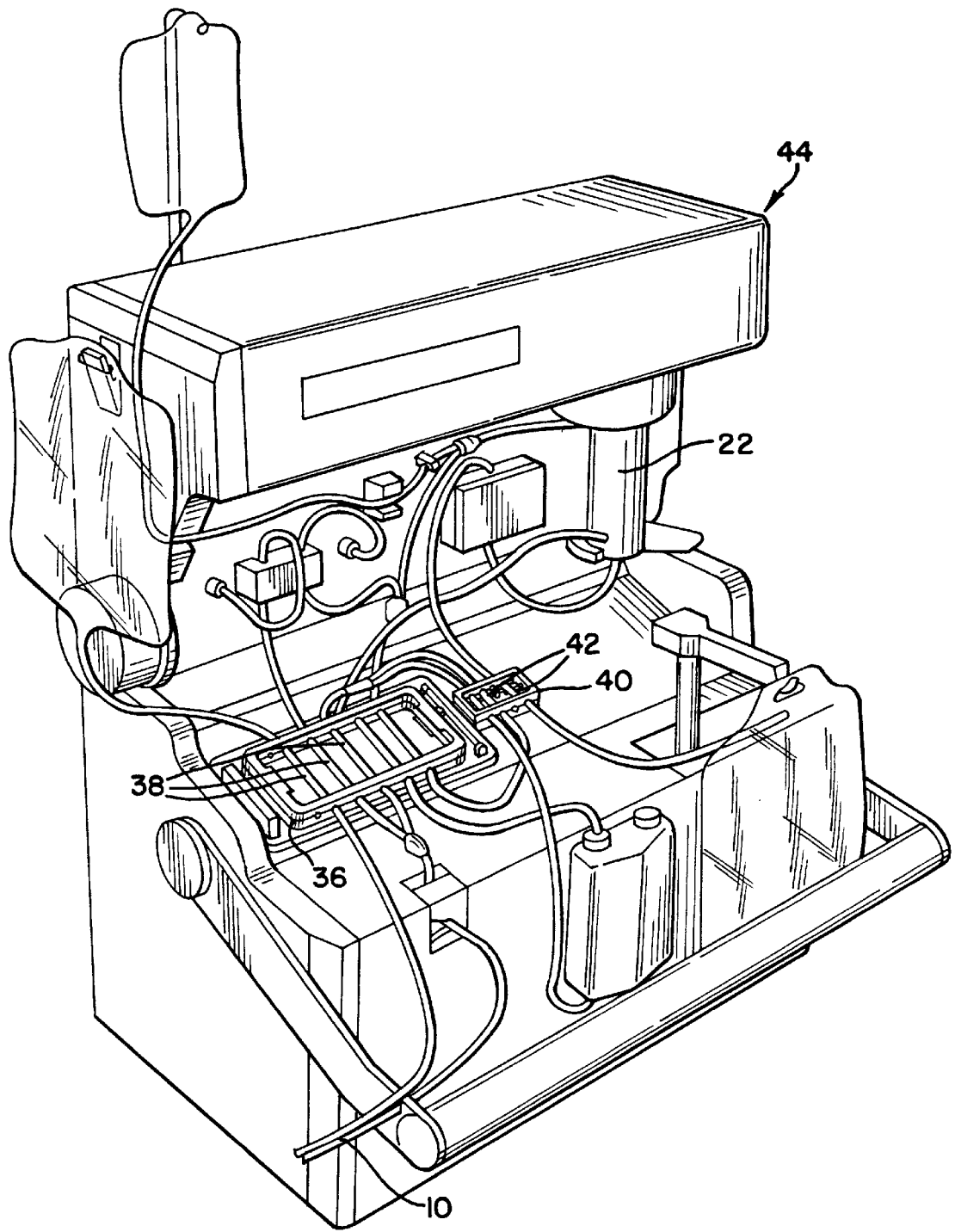
FIG. 2 is a perspective view of a hemapheresis device with a disposable tubing set embodying the present invention installed thereon.
Figure 2A:
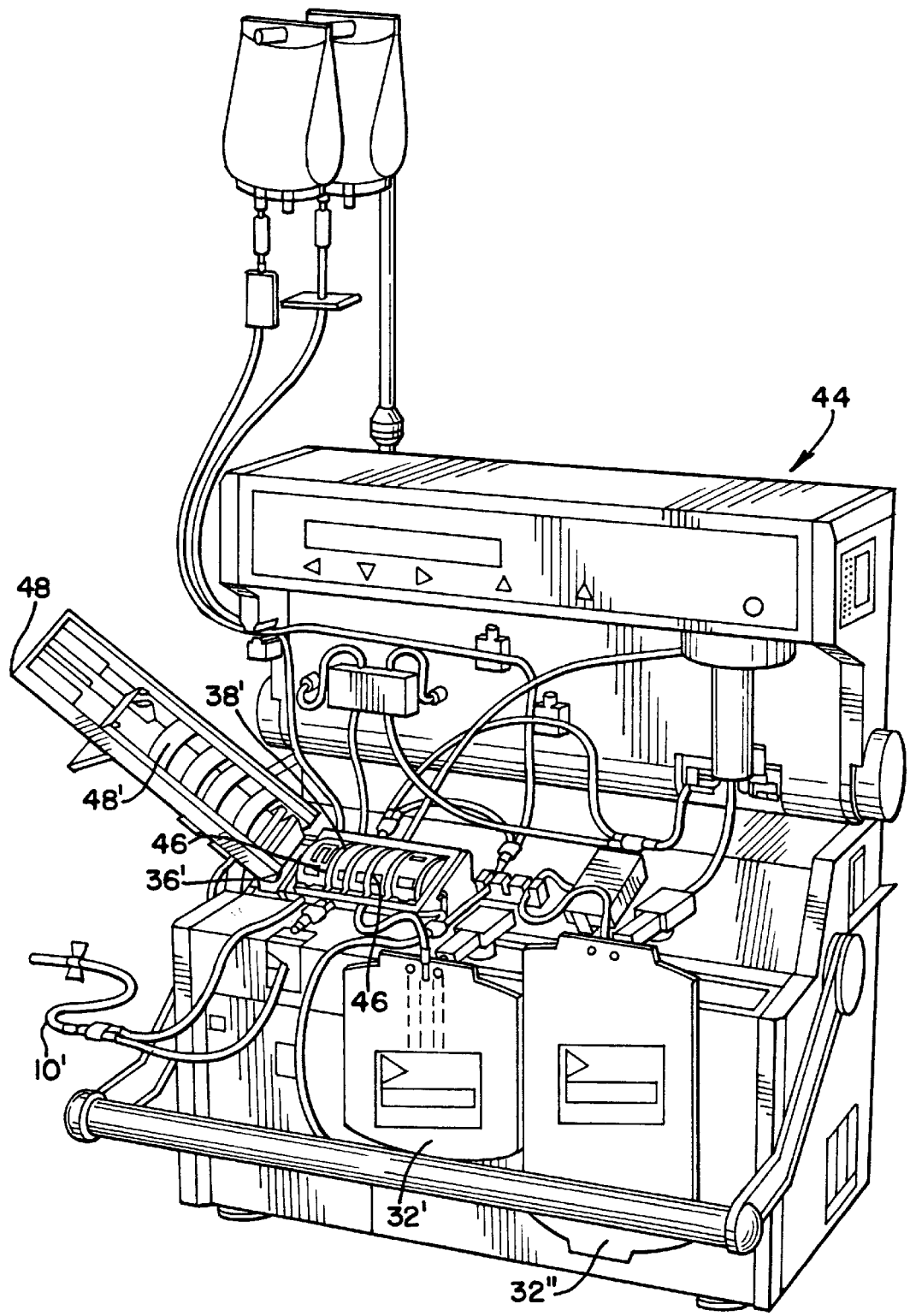
FIG. 2A is a perspective view of a hemapheresis device with an alternative disposable tubing set embodying the present invention installed thereon.

As shown in FIGS. 2 and 2a, disposable tubing sets 10 and 10' are installed on a hemapheresis device 44. As shown, for example, in FIG. 2 (or 2a), tubing organizer 36 (or 36') with tubing segments 38 (38') is installed by placing the organizer 36 over peristaltic pump rotors 46 of hemapheresis device 44. As shown in FIG. 2 and in greater detail in FIG. 3, tubing organizer 40 with tubing segments 42 is placed over clamping device 64 (FIG. 3) of the hemapheresis device 44. The installed tubing segments 38, 38' and 42 may be enclosed by cover 48 (shown, for example, in FIG. 2A) which is pivotally attached to the hemapheresis device 44.

Figure 3:
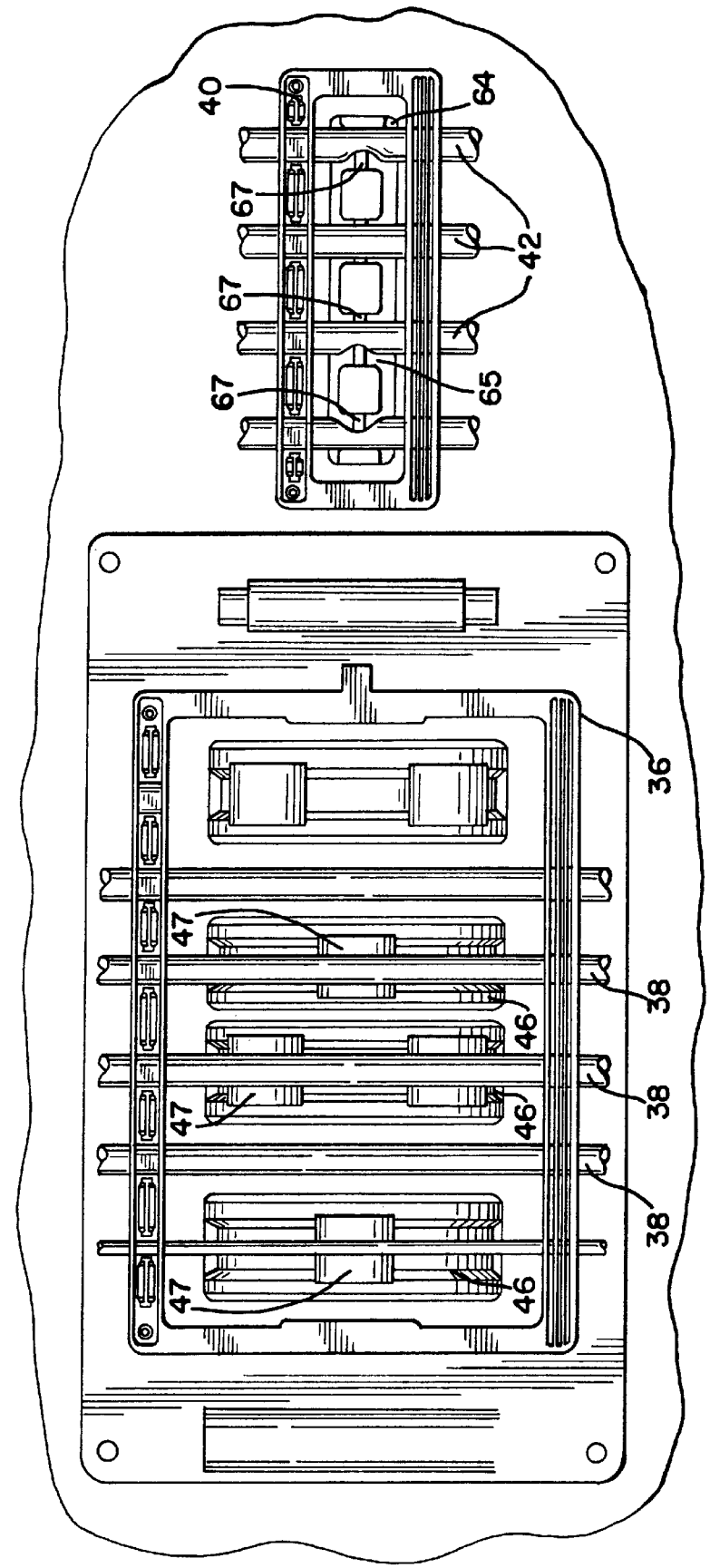
FIG. 3 is a top plan view of tubing organizers embodying the present invention with tubing segments in association with the pump rotors and clamps of a hemapheresis device.
Figure 6:
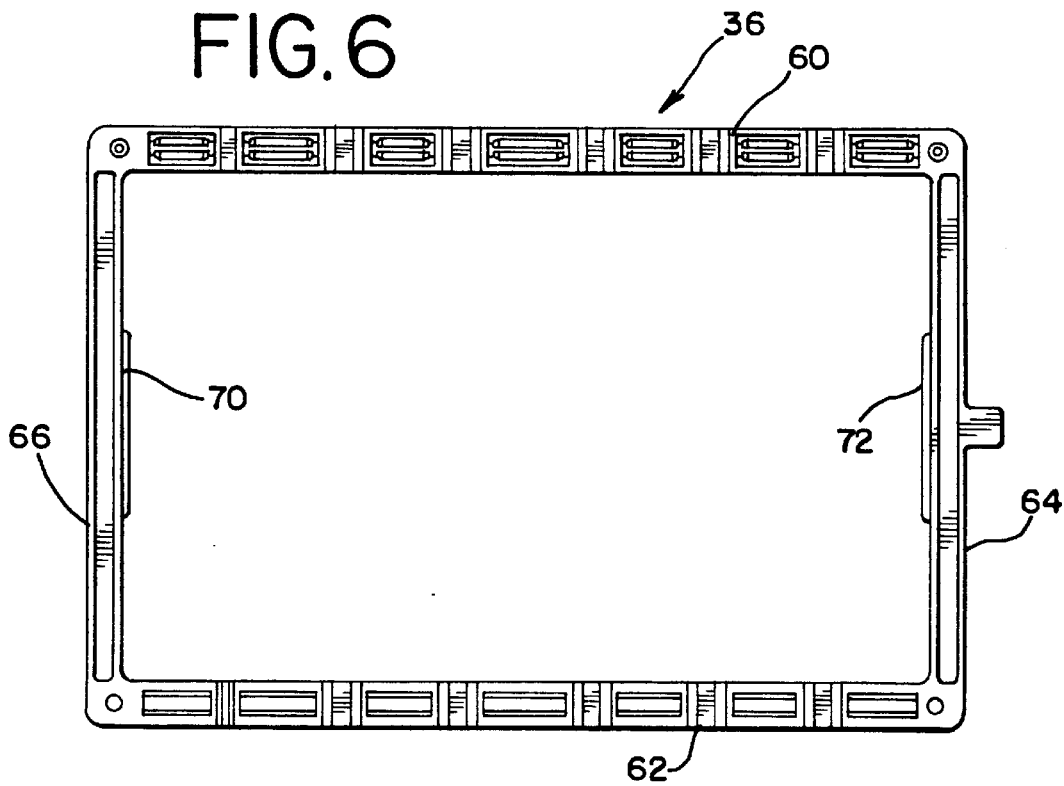
FIG. 6 is a plan view of the tubing organizer of FIG. 4.

More particularly, as shown in FIG. 3, tubing segments 38 are positioned over the pump rotors 46 and more specifically over rollers 47 of pump rotors 46. Pumping of fluid through the tubing is achieved by compression of the tubing segments 38 between rollers 47 and race surfaces 48' shown in FIG. 2A of the hemapheresis instrument. Compression of the tubing segments 38 exerts a force on the tubing and, thereby, pushes blood and/or blood components through the tubing. Also, as shown in FIG. 3, tubing segments 42 held by organizer 40 are positioned within slots 65 of clamping device 64, which includes clamp fingers 67. Clamp fingers 67 can be controlled to clamp off tubing segments 42 (and the flow of fluid therethrough) as desired. A detailed description of the hemapheresis device and its operation, including the peristaltic pump rotors 46, clamping device 64 and the cover 48 is beyond the scope of the present invention, but is included in U.S. Pat. Nos. 5,460,493 and 5,443,451 which are incorporated by reference herein.

Although the following discussion is directed to tubing organizer 36, shown in FIG. 4, it is also applicable to the (smaller) tubing organizer 40 shown in FIGS. 5, 9–11, 17–20 as well as the alternative embodiment of the tubing organizer shown in FIGS. 21–24, 27–28.

As shown in FIG. 4, tubing organizer 36 is a rectangularly shaped frame defined by sides 60, 62, 64 and 66. Sides 60 and 62 include apertures 68 through which tubing segments 38 (shown in broken lines) extend. Tabs 70 and 72 located on the inside edges of sides 64 and 66 of tubing organizer 36 are provided to snap into mating recesses of the pump assembly as shown and described in detail in U.S. Pat. No. 5,460,493.

Tubing organizer 36 may be formed of any suitable material, although a polymeric plastic material is preferred. Suitable polymeric materials for the tubing organizers are any polymers, including the engineering grade polymers which are known to those skilled in the art. However, a general purpose polymer is preferred because of its lower cost and greater flexibility which makes the organizer less susceptible to breaking (during, for example, loading). One such general purpose polymer is acrylonitrile butadiene styrene (ABS) sold under the trademark LUSTRAN® by Monsanto Company of St. Louis, Mo.

Although tubing organizer 36 can be made of one piece construction, as shown in FIG. 12, it is preferred that tubing organizer 36 be formed of two portions 74 and 76 joined in a mating arrangement described in detail below. Referring to FIG. 12, each of the portions 74 and 76 includes recesses 80 provided in the facing surfaces and spaced along sides 60 and 62. When portions 74 and 76 are joined together, recesses 80 are in registration to form the apertures 68 (as shown in FIG. 4) through which tubing segments 38 extend. The spacing of the recesses from the sides 64 and 66 and from each other will depend on the spacing of the peristaltic pump rotors on the instrument so that the proper tubing is mated with the proper pump rotor.

During assembly of the disposable tubing set, tubing segments 38, shown, for example, by broken lines in FIG. 12, are placed within the recesses 80 of, for example, one portion 76 (or portion 74). It does not matter which portion (74 or 76) is used, as both portions are identical. The other portion 74 (or 76) is then placed over the tubing and the two half portions 74 and 76 are snapped together, thereby completely enclosing tubing segments 38 as shown in FIG. 4. By completely enclosing the tubing segments 38, the chance that tubing segments 38 may become dislodged from tubing organizer 36 is eliminated.

Figure 7:
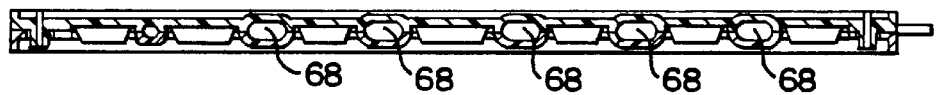
FIG. 7 is a side view of the tubing organizer of FIG. 6.
Figure 8:
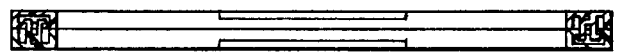
FIG. 8 is an end view of the tubing organizer of FIG. 6.
Figure 9:
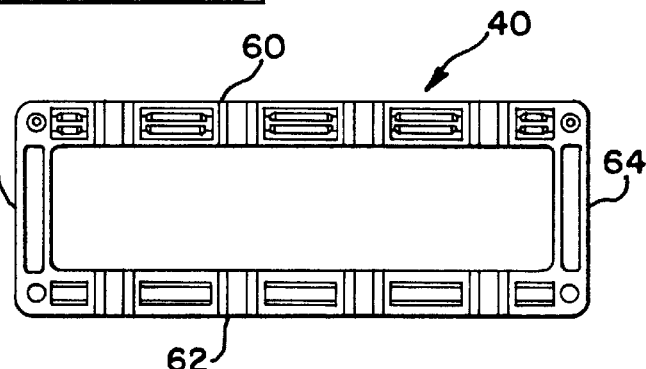
FIG. 9 is a plan view of the tubing organizer of FIG. 5.
Figure 10:
FIG. 10 is a side view of the tubing organizer of FIG. 9.
Figure 11:
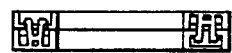
FIG. 11 is an end view of the tubing organizer of FIG. 9.
Figure 17:
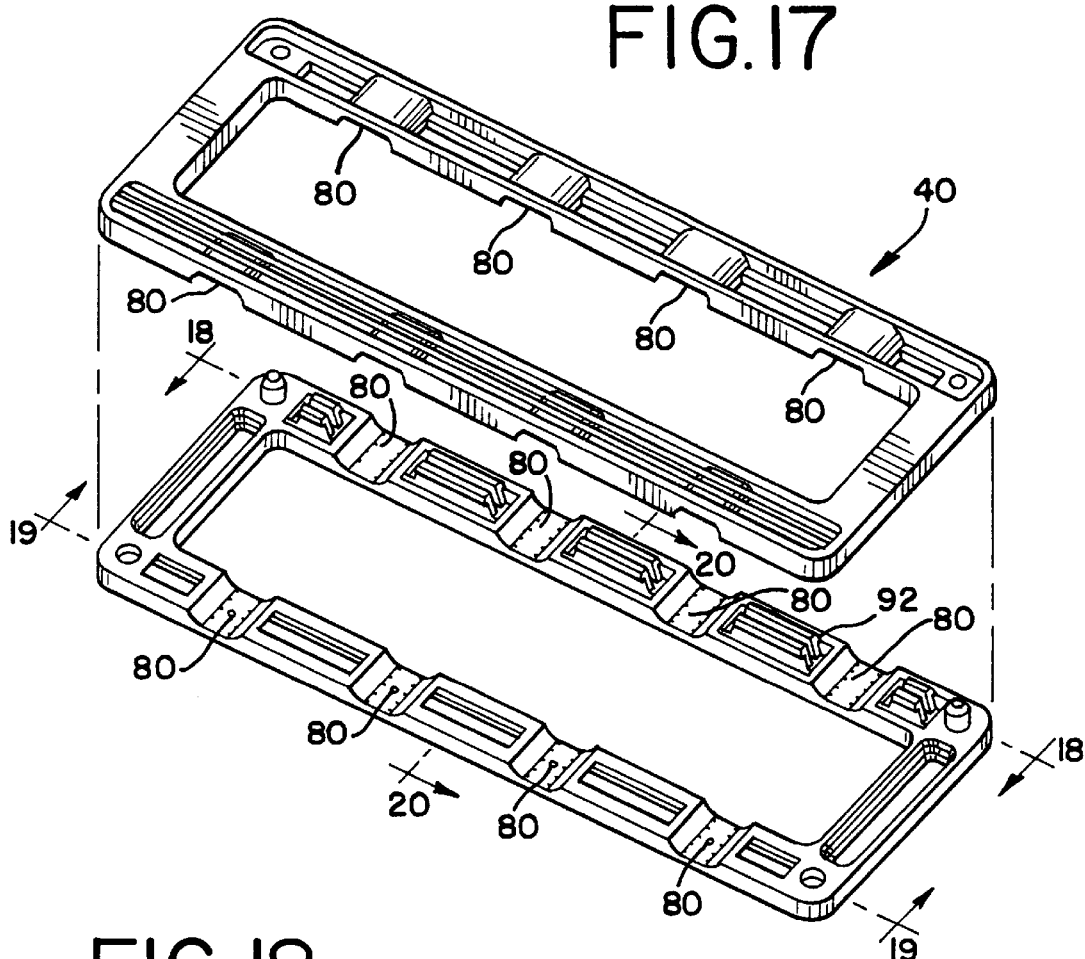
FIG. 17 is an exploded perspective view of the tubing organizer frame of FIG. 5.
Figure 18:
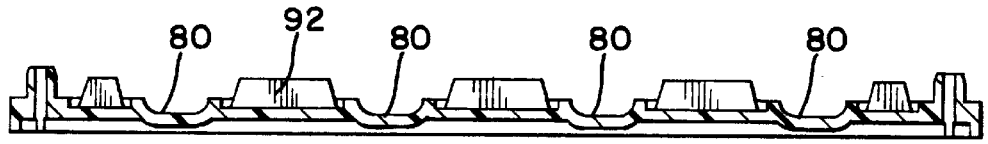
FIG. 18 is a cross-sectional side view of one portion of the tubing organizer of FIG. 17 taken along 18—18.
Figure 19:
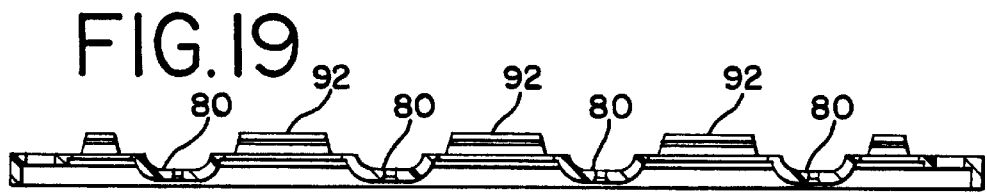
FIG. 19 is a cross-sectional side view of one portion of the tubing organizer of FIG. 17 taken along 19—19.
Figure 20:
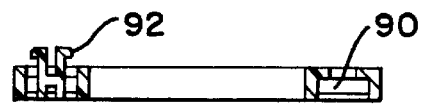
FIG. 20 is a cross-sectional end view of the tubing organizer portion of FIG. 17 taken along 20—20.
Figure 21:
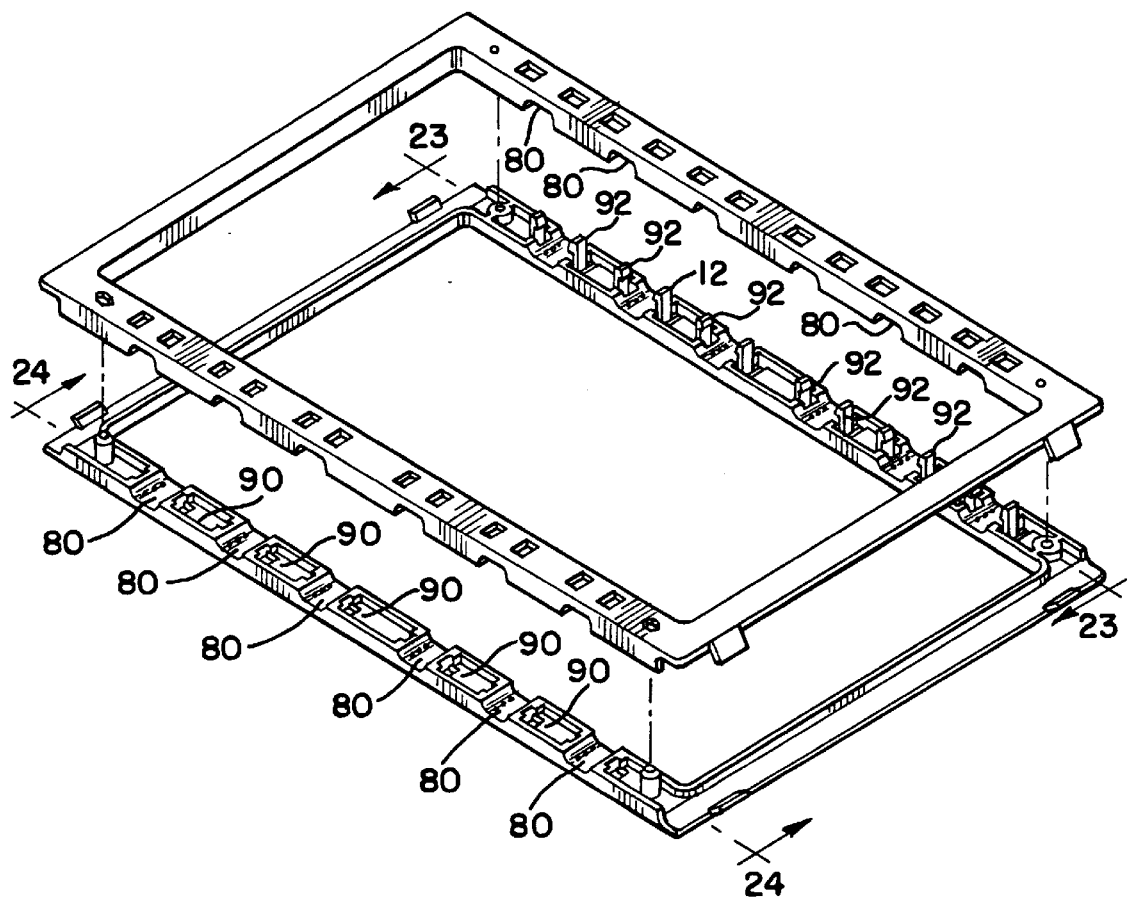
FIG. 21 is an exploded perspective view of an alternative embodiment of the tubing organizer embodying the present invention.
Figure 22:
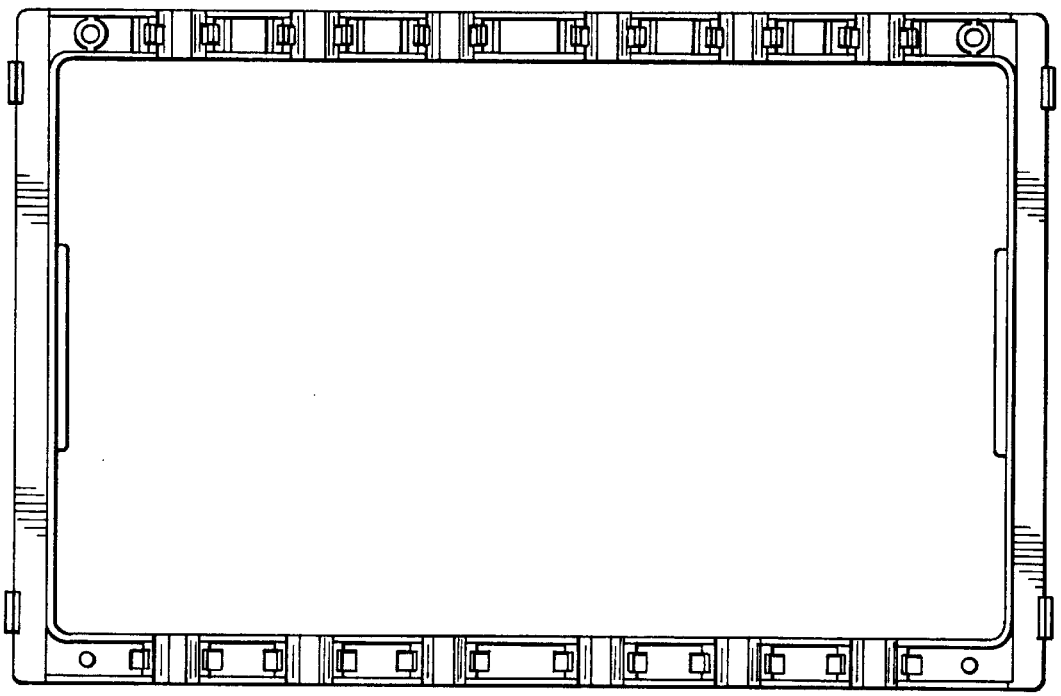
FIG. 22 is a plan view of one portion of the tubing organizer of FIG. 21.
Figure 23:
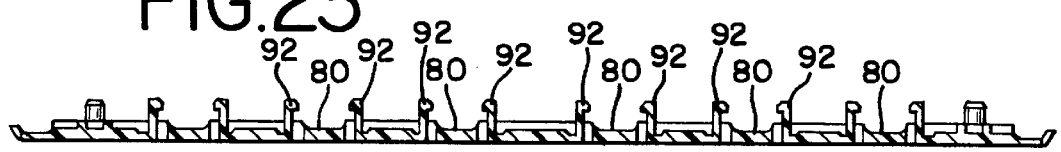
FIG. 23 is a cross-sectional side view of one portion of the tubing organizer of FIG. 21 taken along 23—23.
Figure 24:
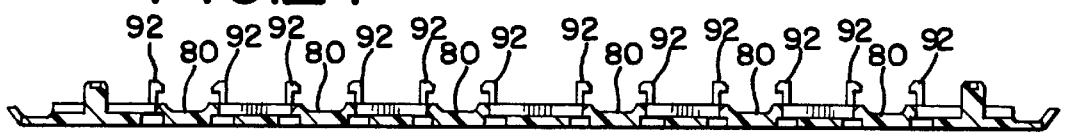
FIG. 24 is a cross-sectional side view of one portion of the tubing organizer of FIG. 21 taken along 24—24.

Aperture(s) 68 formed by recesses 80 has a circumference that is approximately equal to the circumference of the tubing. In one embodiment shown in the figures, apertures 68 are generally oval-shaped, wherein the height (shown as 81 in FIG. 7) is less than the diameter of tubing and the width (shown as 83 in FIG. 7) is greater than the diameter of the tubing. While the shape of the tubing extending through the aperture 68 conforms to the shape of the aperture, there is minimal reduction or change to the cross-sectional area. Thus, the tubing is "gripped" by the aperture without significantly reducing the area of the tubing and without significantly restricting the flow therethrough. Keeping the flow substantially unrestricted reduces the occurrence of hemolysis and lowers operating pressures during an apheresis procedure.

As shown in FIGS. 12 through 20, each portion 74 and 76 of tubing organizer 38 contains a series of slots 90 spaced along one side 62 of the organizer portion between recesses 80 and a series of teeth 92 spaced along the opposite side (e.g. 60) of the organizer portion between recesses 80. In all respects and as set forth above, portions 74 and 76 are identical. Thus, each portion (74 or 76) can be made from the same mold. As shown in FIGS. 25 and 26, when portions 74 and 76 are brought together, teeth 92 of one portion extend through slots 90 of the other portion until beveled tabs 94 of teeth 92 engage the sides 91 of the slots 90 in a snap-locking action. In addition, pins 98 engage holes 100 to align the two portions 74 and 76 and further secure together portions 74 and 76 at each of the four corners of the organizer 36.

An alternative snap locking arrangement is shown in FIGS. 21 through 24 and FIGS. 27–28, where teeth 92 are positioned so that tabs 94 engage the ends 96 of slots 90 rather than the sides.

In one embodiment of the present invention, sides 60 and 62 of organizer 36 are approximately 12 cm (4¾ inches) in length and sides 64 and 66 are approximately 8 cm (3¼ inches) in length. Sides 60 and 62 of organizer 40 are approximately 8 cm (4¾ inches) in length while sides 64 and 66 of organizer 40 are approximately 3 cm in length. Each portion of the tubing organizer 72 or 74 is approximately 0.25 cm (1/16 inch) thick. Recesses 80 are generally concave and may be between approximately 0.2 to 0.6 cm (3/16 to ¼ inch) wide or any width that is at least as large as the diameter of the tubing segment and which allows tubing segments 38, 38' or 42 to be placed within recesses 80 without substantial pinching, stretching or pushing.

Slots 90 may be between approximately 0.8 to 1.2 cm (⅜ to ¼ inch) long and approximately 0.2 to 0.3 cm (3/32 to ⅛ inch) wide. Teeth 92 may be between approximately 0.8 to 1.0 cm (5/16 to ⅜ inch) long and between approximately 0.25 to 0.35 cm (1/16 to ⅛ inch) wide at tabs 94. The distance across tabs 94, indicated by reference numeral 93 in FIGS. 15 and 20, should be slightly wider than slot 90 (the width of which is indicated by reference numeral 95 in FIGS. 15 and 20) so that when inserted through slot 90, tabs 94 firmly engage the sides 91 of slot 90, as shown in FIG. 26, and, thereby, securely join portions 74 and 76.

Of course, these dimensions are provided for illustrative purposes only. The size and dimensions of the tubing organizer will depend on other factors such as the number and diameter of the tubing segments and the location of the mating components (e.g. pump rotors, clamps) on the instrument with which the disposable set 10 (or 10') is used.

While the invention has been described in connection with the foregoing specific embodiments, it is to be understood that the invention is not limited thereto. In fact, as set forth above, the present invention is not limited to tubing sets used in hemapheresis and may be used in a device or system where it is desired to secure tubing to the device or system in a predetermined fashion. Thus, the present invention is intended to cover various modifications and equivalent arrangements included within the spirit and the scope of the appended claims.

That which is claimed:

1. A disposable tubing set comprising:

an array of flexible tubing segments; and a frame for holding said tubing, said frame comprising first and second spaced apart opposed sides, a plurality of apertures defined in said first and second sides, said tubing segments extending through said apertures and being completely enclosed by said apertures at said sides, said frame comprising a first frame portion joined to a second frame portion, said frame portions comprising interfitting teeth and slots.

2. The disposable tubing set of claim 1 further comprising a second frame for holding said tubing, said frame comprising first and second opposed sides, a plurality of apertures defined in said first and second sides, said tubing segments extending through said apertures and being completely enclosed by said apertures.

3. The disposable tubing set of claim 2 wherein said tubing segments extending through said apertures of said second frame are for association with clamps of a hemapheresis instrument.

4. The disposable tubing set of claim 1 wherein said frame comprises a polymeric material.

5. The disposable tubing set of claim 4 wherein said polymeric material comprises acrylonitrile butadiene styrene.

6. The disposable tubing set of claim 1 wherein said tubing set is for use in association with a hemapheresis instrument having peristaltic pumps and clamps for clamping off said tubing.

7. The disposable tubing set of claim 6 wherein said tubing set is used in association with a hemapheresis instrument that separates red cells from whole blood.

8. The disposable tubing set of claim 6 wherein said tubing set is used in association with a hemapheresis instrument that separates plasma from whole blood.

9. The disposable tubing set of claim 1 wherein said tubing segments are for association with peristaltic pumps of a hemapheresis instrument.

10. A method for holding an array of flexible tubing, said method comprising:

providing a first frame portion, said portion comprising a first side and a second side opposite and spaced from said first side, each of said sides having inner surfaces with recesses spaced thereon and wherein said first side comprises teeth and said opposite second side comprises slots;

providing a second frame portion, identical to said first portion;

locating segments of said tubing between the inner surfaces of said first portion and the inner surfaces of said second frame portion so that said tubing segments are disposed within said recesses of said first and second frame portions;

joining said first and second frame portions by inserting said teeth of said first portion side into said slots of said second portion side, said recesses of said first and second portions being in registration to form a closed aperture around said tubing segment.

11. The method of claim 10 wherein said teeth and slots are spaced between said recesses.

12. The method of claim 10 comprising providing first and second frame portions made of a polymeric material.

13. The method of claim 12 wherein said polymeric material comprises acrylonitrile butadiene styrene.

14. The method of claim 10 wherein said recesses have a width not smaller than the diameter of said tubing.

15. A disposable tubing set comprising:

an array of flexible tubing segments; and a frame for holding said tubing, said frame comprising first and second spaced apart opposed sides, a plurality of apertures defined in said first and second sides, said tubing segments extending through said apertures and being completely enclosed by said apertures, said frame comprising a first frame portion joined to an identical second frame portion, each of said frame portions comprising interfitting teeth and slots.

16. A disposable tubing set comprising:

an array of flexible tubing segments; and a frame for holding said tubing, said frame comprising first and second spaced apart opposed sides, a plurality of apertures defined in said first and second sides, said tubing segments extending through said apertures and being completely enclosed by said apertures, said frame comprising a first frame portion joined to an identical second frame portion.

17. The disposable tubing set of claim 16 wherein said frame comprises a polymeric material.

\* \* \* \* \*